United States Patent [19]

Kroenke

[11] 4,425,279
[45] Jan. 10, 1984

[54] TRIDODECYLAMMONIUM MOLYBDATES

[75] Inventor: William J. Kroenke, Brecksville, Ohio

[73] Assignee: The B. F. Goodrich Company, Akron, Ohio

[21] Appl. No.: 402,482

[22] Filed: Jul. 28, 1982

[51] Int. Cl.$^3$ .............................................. C07F 11/00
[52] U.S. Cl. ................................ 260/429 R; 524/204; 524/567
[58] Field of Search .................................... 260/429 R

[56] References Cited

U.S. PATENT DOCUMENTS 4,248,766  2/1981  Kroenke ...................... 260/429 R X
4,248,767  2/1981  Kroenke ...................... 260/429 R X Primary Examiner—Helen M. S. Sneed
Attorney, Agent, or Firm—James R. Lindsay

[57] ABSTRACT

Tridodecylammonium molybdates having the empirical formula $$[(C_{12}H_{25})_3NH]_a Mo_b O_c$$

where a, b and c are (2,6,19); (6,7,24) or (4,8,26) are disclosed as novel amine molybdates which are useful as smoke retardant additives for vinyl chloride polymer compositions.

3 Claims, No Drawings

TRIDODECYLAMMONIUM MOLYBDATES

BACKGROUND OF THE INVENTION

Amine molybdates may be produced by reacting an amine or an amine salt with a molybdenum compound such as molybdenum trioxide ($MoO_3$), molybdic acid or a molybdenum salt in an acidic aqueous medium made acidic through the addition of a suitable acid such as an inorganic acid (exemplified by hydrochloric acid, nitric acid or sulfuric acid) or an organic acid containing 1 to 12 carbon atoms (exemplified by acetic acid, propionic acid, benzoic acid, and the like). The acidic mixture is refluxed, preferably while being stirred continuously, until the reaction is complete, usually for about ¼ to 4 hours.

Amine molybdates also may be produced, as described in U.S. Pat. No. 4,217,292, by reacting essentially stoichiometric quantities of molybdenum trioxide with an amine or an amine salt in an aqueous medium essentially free of acid and in which a water-soluble ammonium or monovalent metal or divalent metal or trivalent rare earth metal salt of an inorganic or organic acid is dissolved. Sometimes the reaction is carried out in a polar organic solvent instead of water.

The particular amine molybdate formed may depend upon which process is used to form the amine molybdate and the quantity of reactants present in the reaction mixture, as well as the reaction conditions.

SUMMARY OF THE INVENTION

The present invention pertains to a class of novel molybdates, namely, tridodecylammonium molybdates, which may be represented by the formula:

$$[(C_{12}H_{25})_3NH]_aMo_bO_c$$

where a, b and c are (2,6,19); (6,7,24) or (4,8,26). Like many other amine molybdates, the tridodecylammonium molybdates function as effective smoke retardant additives for vinyl chloride polymers.

DETAILED DESCRIPTION OF THE INVENTION

Tridodecylammonium molybdates may be produced by reacting ammonium dimolybdate [$(NH_4)_2Mo_2O_7$] and tridodecylamine [$(C_{12}H_{25})_3N$] in an acidic aqueous medium. Suitable acids include inorganic acids, such as hydrochloric acid, nitric acid, sulfuric acid, and the like, or mixtures thereof. The amount of acid used may be varied widely from about ½ to 10 or more molar equivalents of acid per molar equivalent of ammonium dimolybdate. However, about a 1/1 molar equivalent ratio is preferred. Sufficient water is included in the reaction mixture to insure a reaction medium that has a consistency that enables it to be easily stirred. Since tridodecylamine and the tridodecylammonium molybdates of the present invention are insoluble in an aqueous medium, preferably, the ammonium dimolybdate is dissolved in the aforementioned aqueous medium while the tridodecylamine is dissolved in an organic solvent that is a solvent both for the tridodecylamine of the reaction mixture and for the amine molybdate reaction product and that is immiscible in water (benzene, toluene, methylene chloride, methanol or cyclohexane, for example). The two immiscible solutions are mixed together and heated to reflux while being stirred. The reaction materials are refluxed while being stirred continuously for about 0.25 to 16 hours, preferably at a temperature between 75° to 110° C. The tridodecylammonium molybdate reaction product remains dissolved in the organic solvent phase of the mixture. After the reaction is completed, the two immiscible factions are separated from each other. The organic solvent phase, containing the tridodecylammonium molybdate, desirably is washed with water and dried over an appropriate desiccant, such as calcium hydride. If desired, the organic solvent can be removed from the tridodecylammonium molybdate by evaporation or distallation. The molar ratio of ammonium dimolybdate to tridodecylamine will influence the tridodecylammonium molybdates formed as a result of the reaction. Theoretical molybdenum/tridodecylamine molar ratios from 0.5/1 to 3/1 are used. However, the actual molar ratios that can be used in the reaction can be outside the stated range, but generally will produce mixtures of the molybdates. The tridodecylammonium molybdates within the scope of the present invention are tridodecylammonium hexamolybdate [$(C_{12}H_{25})_3NH]_2Mo_6O_{19}$, tridodecylammonium heptamolybdate [$(C_{12}H_{25})_3NH]_6Mo_7O_{24}$ and tridodecylammonium octamolybdate [$(C_{12}H_{25})_3NH]_4Mo_8O_{26}$.

The following examples more fully illustrate the preparation of the novel tridodecylammonium molybdates of the present invention.

EXAMPLE I 3.91 grams of ammonium dimolybdate were dissolved in 180 milliliters of water. The solution was added to a 1000 milliliter round-bottom flask equipped with a water-cooled condenser and a mechanical stirrer. 2.27 grams of a 37 percent hydrochloric acid solution were added to the flask with 45 milliliters of water. 6.00 grams of tridodecylamine were dissolved in 200 milliliters of cyclohexane and were added to the flask with an additional 25 milliliters of cyclohexane. The reaction mixture in the flask was heated to reflux and refluxed while being stirred continuously for ½ hour. The contents of the flask were cooled to room temperature (about 25° C.) and transferred into a separatory funnel. The aqueous phase was removed from the separatory funnel, leaving the cyclohexane phase in which the amine molybdate reaction product is dissolved remaining. The cyclohexane phase was washed three times with 25 milliliters of water, separating the wash water from the cyclohexane phase after each washing. The cyclohexane phase then was dried over 3 A molecular sieves. The yellow-colored product remaining as a residue after evaporating the cyclohexane from a sample of the cyclohexane phase was identified by infrared analysis to be tridodecylammonium alpha-octamolybdate.

EXAMPLE II 5.00 grams of tridodecylamine were added to a 250 milliliter round-bottom flask equipped with a water-cooled condenser and a mechanical stirrer. 50 milliliters of methanol then was added to the flask, followed by the addition (in the order stated) of 4.88 grams of ammonium dimolybdate, 25 additional milliliters of methanol, 2.83 grams of a 37 percent hydrochloric acid solution mixed into 25 milliliters of methanol, and a final addition of 25 milliliters of methanol. The cloudy mixture in the flask was heated to reflux and refluxed while being stirred continuously for 25 minutes. As the mixture was heated, it first became yellow in color and then changed to green in color. The contents of the flask were cooled to room temperature (about 25° C.). White particles of ammonium chloride and a viscous dark green mass were observed in the methanol medium. The methanol was poured off the green mass. The mass then was washed three times with methanol, decanting off the methanol wash after each washing. The green reaction product was dried in a vacuum oven at 40° C. overnight (approximately 16 hours) and was dissolved in 45 milliliters of methylene chloride. The solution which contained particles of ammonium chloride was filtered to remove the ammonium chloride from the solution. After evaporating the methylene chloride from a sample of the solution, the dark green residue was identified by infrared analysis to be tridodecylammonium hexamolybdate.

EXAMPLE III 3.91 grams of ammonium dimolybdate were dissolved in 180 milliliters of water. The solution was added to a 1000 milliliter round-bottom flask equipped with a water-cooled condenser and a mechanical stirrer. 2.27 grams of a 37 percent hydrochloric acid solution were added to the flask with 45 milliliters of water. 6.00 grams of tridodecylamine were dissolved in 200 milliliters of methylene chloride and were added to the flask with an additional 25 milliliters of methylene chloride. The reaction mixture in the flask was heated to reflux and refluxed while being stirred continuously for 1 hour. The contents of the flask were cooled to room temperature (about 25° C.) and transferred into a 1000 milliliter separatory funnel. The aqueous layer was removed from the separatory funnel, leaving the methylene chloride layer in which the amine molybdate reaction product is dissolved. The methylene chloride phase was washed three times with 25 milliliters of water, separating the wash water from the methylene chloride phase after each washing. The methylene chloride phase was dried over 3 A molecular sieves. The yellow-colored residue remaining after evaporating the methylene chloride from a sample of the methylene chloride phase was identified by infrared analysis to be tridodecylammonium beta-octamolybdate.

The tridodecylammonium molybdates have been found to be a smoke retardant additive for vinyl chloride polymer compositions. When used as a smoke retardant additive, the tridodecylammonium molybdates desirably are dissolved in an organic solvent for the molybdate (such as methylene chloride) and mixed with the dry vinyl chloride polymer particles. The methylene chloride then is allowed to evaporate from the vinyl chloride polymer leaving the tridodecylammonium molybdate deposited on the vinyl chloride polymer particles. Preferably, from about 0.1 to about 20 parts by weight of a tridodecylammonium molybdate is used per 100 parts by weight of vinyl chloride polymer.

Vinyl chloride polymers with which the tridodecylammonium molybdates can be used as smoke retardant additives include homopolymers, copolymers and blends of homopolymers and/or copolymers, and include chlorinated polymers thereof. The vinyl chloride polymers may contain from 0 to 50 percent by weight of at least one other olefinically unsaturated monomer. Suitable monomers include 1-olefins containing from 2 to 12 carbon atoms such as ethylene, propylene, 1-butene, isobutylene, 1-hexene, 4-methyl-1-pentene, and the like; dienes containing from 4 to 10 carbon atoms, including conjugated dienes such as butadiene, isoprene, piperylene, and the like; ethylidene norbornene and dicyclopentadiene; vinyl esters and allyl esters such as vinyl acetate, vinyl chloroacetate, vinyl propionate, vinyl laurate, alkyl acetate, and the like; vinyl aromatics such as stryene, α-methyl styrene, chlorostyrene, vinyl toluene, vinyl naphthalene, and the like; vinyl allyl ethers and ketones such as vinyl methyl ether, allyl methyl ether, vinyl isobutyl ether, vinyl n-butyl ether, vinyl chloroethyl ether, methylvinyl ketone, and the like; vinyl nitriles such as acrylonitrile, methacrylonitrile, and the like; cyanoalkyl acrylates such as α-cyanomethyl acrylate, the α-β- and α-cyanopropyl acrylate, and the like; olefinically unsaturated acids and esters thereof including α,β-olefinically unsaturated acids and esters thereof such as methyl acrylate, ethyl acrylate, chloropropyl acrylate, butyl acrylate, hexyl acrylate, 2-ethylhexyl acrylate, dodecyl acrylate, octadecylacrylate, methoxyethyl acrylate, ethoxyethyl acrylate, hexylthioethyl acrylate, methyl methacrylate, ethyl methacrylate, butyl methacrylate, and the like.

The vinyl chloride polymer, in addition to the tridodecylammonium molybdate, may contain the usual compounding ingredients known to the art such as fillers, stabilizers, opacifiers, lubricants, processing aids, impact modifiers, plasticizers, antioxidants, and the like.

Smoke retardancy may be measured using an NBS Smoke Chamber according to procedures described in ASTM E662-79 "Test For Specific Optical Density Of Smoke Generated By Solid Materials". Maximum smoke density (Dm) is a dimensionless number and has the advantage of representing a smoke density independent of chamber volume, specimen size or photometer path length, provided a consistent dimensional system is used. Percent smoke reduction is calculated using the equation:

$$\frac{Dm/g \text{ of control} - Dm/g \text{ of sample}}{Dm/g \text{ of control}} \times 100$$

The term "Dm/g" means maximum smoke density per gram of material. Dm and other aspects of the physical optics of light transmission through smoke are discussed fully in the ASTM publication.

The smoke retardant property of tridodecylammonium molybdates is illustrated by the following examples:

EXAMPLE IV

The following recipe was used:

| Material | Parts by Weight |
| --- | --- |
| Polyvinyl Chloride resin* | 100.0 |
| Lubricant** | 2.0 |
| Tin Stabilizer*** | 2.0 |
| Tridodecylammonium molybdate | 5.0 |

*Homopolymer of vinyl chloride having an inherent viscosity of about 0.98–1.04; ASTM classification GO-5-15543.
**A commerical polyethylene powder lubricant (Microthene 510).
***Tin Thioglycolate 5.0 grams of the tridodecylammonium alphaoctamolybdate of Example I, dissolved in 135 milliliters of cyclohexane, were slowly added with constant stirring to 100 grams of the polyvinyl chloride resin contained in a porcelain dish heated in a water bath maintained at about 50° to 60° C. Mixing was continued until the polyvinyl chloride resin appeared to be dry. The molybdate-polyvinyl chloride resin mixture was heated in a vacuum oven maintained at 40° C. until the cyclohexane was evaporated from the sample. The lubricant and tin stabilizer of the recipe were added to the molybdate-polyvinyl chloride resin mixture and the resulting composition was milled on a two-roll mill for about 5 minutes at a roll temperature of about 165° C. The milled composition was pressed into a 6×6×0.05 inch sheet. Pressing was done at about 160° C. for 5 minutes using 40,000 pounds (about 14,900 kg) of force applied to a 4-inch ram. The sample (Sample 1) received a 2 minute preheat before being pressed.

5.0 grams of the tridodecylammonium hexamolybdate of Example II, dissolved in 235 milliliters of methylene chloride, were mixed with constant stirring to 100 grams of polyvinyl chloride resin in a porcelain dish heated in a water bath maintained at 40° C. Mixing was continued while heating the mixture to about 45° C. until the polyvinyl chloride resin appeared to be dry. The resulting molybdate-polyvinyl chloride resin mixture was heated in a vacuum oven maintained at 40° C. until the methylene chloride was evaporated from the sample. The other ingredients of the aforesaid recipe were combined with the molybdate-polyvinyl chloride resin mixture and the resulting composition pressed into a test sample (Sample 2) as described above.

5.0 grams of the tridodecylammonium beta-octamolybdate of Example III, dissolved in 255 milliliters of methylene chloride, were mixed with constant stirring to 100 grams of polyvinyl chloride resin in a porcelain dish heated in a water bath maintained at 40° C. Mixing was continued while heating the mixture until the polyvinyl resin appeared to be dry. The resulting molybdate-polyvinyl chloride resin mixture was heated in a vacuum oven maintained at about 45° C. until the methylene chloride was evaporated from the sample. The other ingredients of the aforesaid recipe were combined with the molybdate-polyvinyl chloride resin mixture and the resulting composition pressed into a test sample (Sample 3) as described above.

The molded samples were cut into $2\frac{7}{8} \times 2\frac{7}{8} \times 0.50$ inch sections and tested against a control sample formed utilizing the aforesaid recipe but without use of the molybdate additive. Testing was performed using the flaming mode of the NBS Smoke Chamber Test (ASTM E662-79) described hereinabove. The test results are given in Table I.

TABLE I

| Sample | Dm/g* | Smoke Reduction (%) |
|---|---|---|
| Control | 63.0 | — |
| 1 | 42.9 | 32.0 |
| 2 | 43.4 | 31.2 |
| 3 | 40.7 | 35.3 |

*Dm/g = maximum smoke density per gram of sample.

The improved smoke retardant vinyl chloride polymer compositions obtained by the inclusion of a tridodecylammonium molybdate in the composition are useful wherever smoke reduction is a desirable property, such as in carpeting, house siding, plastic components for aircraft and passenger car interiors, and the like.

I claim:

1. Tridodecylammonium molybdates having the empirical formula $$[(C_{12}H_{25})_3NH]_a Mo_b O_c$$

where a, b and c are (2,6,19) or (4,8,26).

2. The tridodecylammonium molybdate of claim 1 wherein a is 2, b is 6, and c is 19.

3. The tridodecylammonium molybdate of claim 1 wherein a is 4, b is 8, and c is 26.

* * * * *